(12) United States Patent
Kirsammer et al.

(10) Patent No.: US 11,668,675 B2
(45) Date of Patent: Jun. 6, 2023

(54) MEASURING DEVICE

(71) Applicant: Siemens Aktiengesellschaft, Munich (DE)

(72) Inventors: Florian Kirsammer, Karlsruhe (DE); Benjamin Schmidt, Karlsruhe (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 17/373,331

(22) Filed: Jul. 12, 2021

(65) Prior Publication Data

US 2022/0011267 A1 Jan. 13, 2022

(30) Foreign Application Priority Data

Jul. 13, 2020 (EP) .................................. 20185402

(51) Int. Cl.
*G01N 27/74* (2006.01)
*G01N 33/00* (2006.01)

(52) U.S. Cl.
CPC ......... *G01N 27/74* (2013.01); *G01N 33/0036* (2013.01)

(58) Field of Classification Search
CPC ... G01D 3/0365; G01N 27/74; G01N 33/0036
See application file for complete search history.

(56) References Cited

U.S. PATENT DOCUMENTS 6,498,996 B1 * 12/2002 Vallot .................... G01C 21/16
702/56

2008/0140316 A1 * 6/2008 Masson ................ G01C 25/005
701/510

(Continued)

FOREIGN PATENT DOCUMENTS

| CN | 108200773 A | 6/2018 |
| CN | 110749337 A | 2/2020 |

(Continued)

OTHER PUBLICATIONS

Pan, Xinmin et al; "Computer Techniques in Materials Science and Engineering"; China University of Mining and Technology Press; Publication Date Dec. 31, 2000; (pp. 80-81); 2000.

*Primary Examiner* — Jermele M Hollington
*Assistant Examiner* — Suresh K Rajaputra
(74) *Attorney, Agent, or Firm* — Henry M. Feiereisen LLC

(57) ABSTRACT

A measuring device includes a sensor generating a sensor signal in dependence upon a detected measured variable, a compensating facility generating a compensation signal in response to detected shocks, and an evaluating facility generating a measurement result from a difference between the sensor signal and the compensation signal. The compensating facility includes a multi-axis MEMS inertial measuring unit having an acceleration sensor alone or together with a gyroscope and generating a plurality of movement signals in correspondence to a number of axes, and a computer including a computational model trained to model an unwanted signal portion of the sensor signal in response to the shocks caused by the movement signals, and to output the unwanted signal portion as a compensation signal. The computational mod& is trained such that absent a measured variable, the difference between the sensor signal and the compensation signal is zero or is below a predetermined threshold.

6 Claims, 2 Drawing Sheets

(56) References Cited

U.S. PATENT DOCUMENTS

| | | | |
|---|---|---|---|
| 2009/0249521 A1* | 10/2009 | Dazzi | B82Y 35/00 |
| | | | 356/51 |
| 2010/0161268 A1* | 6/2010 | Gottfriedsen | G01G 23/10 |
| | | | 702/101 |
| 2010/0188149 A1 | 7/2010 | Kimmig et al. | |
| 2017/0336228 A1* | 11/2017 | Grossman | G01C 21/183 |
| 2018/0023840 A1 | 1/2018 | Yamaji | |
| 2018/0034413 A1 | 2/2018 | Kirsammer et al. | |
| 2018/0149506 A1 | 5/2018 | Wiest et al. | |
| 2018/0286425 A1 | 10/2018 | Baek et al. | |

FOREIGN PATENT DOCUMENTS

| | | |
|---|---|---|
| DE | 27 02 978 A1 | 8/1977 |
| DE | 196 48 241 A1 | 7/1997 |
| EP | 2 130 295 A1 | 12/2009 |
| EP | 3187840 A1 | 7/2017 |
| EP | 3 246 661 A1 | 11/2017 |
| EP | 3 276 308 A1 | 1/2018 |
| JP | H08233643 A | 9/1996 |
| JP | H0996557 A | 4/1997 |
| JP | 2013002941 A | 1/2013 |
| JP | 6439860 B2 | 12/2018 |
| KR | 20000058384 A | 10/2000 |
| KR | 20180111271 A | 10/2018 |

\* cited by examiner

MEASURING DEVICE

CROSS-REFERENCES TO RELATED APPLICATIONS

This application claims the priority of European Patent Application, Serial No. EP 20185402.3, filed Jul. 13, 2020, pursuant to 35 U.S.C. 119(a)-(d), the disclosure(s) of which is/are incorporated herein by reference in its entirety as if fully set forth herein.

BACKGROUND OF THE INVENTION

The present invention relates to a shock-sensitive measuring device.

The following discussion of related art is provided to assist the reader in understanding the advantages of the invention, and is not to be construed as an admission that this related art is prior art to this invention.

MEMS acceleration sensors and gyroscopes for detecting movements in drones, mobile telephones, motor vehicles, aircraft and mobile internet of things (IoT) devices are generally known. 3D acceleration sensors measure linear accelerations along three orthogonal axes, however they do not react to angular velocities, 3D gyroscopes measure angular velocities about the axes, however they do not react to linear accelerations. Sensor fusion technology could be used to combine results of the two sensors in order to obtain an image of the movement.

Also known are micro flow sensors or thermal conductivity detectors such as those used in gas analysis, wherein metal threads or meandering metal meshes are used as sensor elements because only such fine structures have a sufficiently low thermal capacity and render possible the required measuring sensitivity. However, the mechanical sensitivity of free-hanging metal threads that sag during heating, so that the serviceable life and the measurement accuracy during vibrations are adversely affected.

It would be desirable and advantageous to provide an improved measuring device to obviate prior art shortcomings and to reduce susceptibility to interference of a measuring device with respect to vibrations and shocks in a simple manner.

SUMMARY OF THE INVENTION

According to one aspect of the invention, a shock-sensitive measuring device includes a sensor generating a sensor signal in dependence upon a detected measured variable, a compensating facility generating a compensation signal in response to detected shocks of the measuring device, and an evaluating facility generating a measurement result from a difference between the sensor signal and the compensation signal, wherein the compensating facility includes a multi-axis MEMS inertial measuring unit including an acceleration sensor alone or together with a gyroscope and configured to generate a plurality of movement signals in correspondence to a number of axes, and a computer including a computational model embodied and trained to model an unwanted signal portion of the sensor signal in response to the shocks caused by the movement signals and to output the unwanted signal portion as a compensation signal, with the computational model being trained in such a manner that absent a measured variable, the difference between the sensor signal and the compensation signal is zero or is below a predetermined threshold.

A multi-axis MEMS inertial measuring unit offers a sufficient bandwidth and resolution in order to detect shocks within the measuring device. Owing to its particularly small size, it is possible for the measuring unit to be positioned particularly closely to the sensor with the result that in the event of shocks, vibrations or the like, the measuring unit performs approximately the same movement as the sensor. The terra "movement signals" is understood to mean the acceleration signals of the acceleration sensor and the angular velocity signals of the gyroscope, wherein the acceleration signals can be converted by integration into velocity signals. The movement signals that are provided by the measuring unit for the different rotational axes of the gyroscope and the acceleration axes of the acceleration sensor are converted by means of the computational model into the one-dimensional unwanted signal portion of the sensor signal, with the unwanted signal portion caused by the shocks. In order to learn the mapping of the movement signals that are provided by the MEMS inertial measuring unit in response to the influence of the sensor signal, it is possible prior to bringing the measuring device into operation for the measuring device to be purposefully excited using oscillations or vibrations outside the measuring operation or in measuring pauses in which the sensor does not detect a measured variable, for example is shielded from the measured variable, wherein the mapping rule is adapted in such a manner that the difference between the sensor signal and the calculated compensation signal is zero or is below a predetermined threshold.

The learning procedure or training procedure can be performed simultaneously for all movement signals that are provided by the MEMS inertial measuring unit. According to another advantageous feature of the invention, the computational model can include for this purpose a neural network that obtains the movement signals as input variables and generates as output variables an estimation of the one-dimensional unwanted signal portion of the sensor signal, which unwanted signal portion is caused as a result of the shocks. Such a neural network may, optionally, also be embodied from part networks, e.g. for the movement signals of the acceleration sensor and the movement signals of the gyroscope, with the output variables of the part networks being combined.

The computational complexity for the training of the computational model can be reduced in that the shock-caused unwanted signal portion of the sensor signal is learned separately in the learning or training phase for each movement signal, i.e. for each acceleration axis of the acceleration sensor and, optionally, for each axis of rotation of the gyroscope. According to another advantageous feature of the invention, the computational model can include for this purpose for each of the movement signals a digital filter that is trained via a setting of the filter coefficient of the digital filter to model a shock-caused unwanted signal portion of the sensor signal in correlation with the relevant movement signal. The output signals of the filters can then be combined to generate the compensation signal during the measuring operation through simple addition.

In general, the analog sensor signal can be filtered and/or amplified in a signal preprocessing facility prior to digitization of the sensor signal and processed in a digital signal processing facility using signal processing software to produce the measurement result. The digital signal processing steps can contain for example a digital filtering procedure, a specification of the zero point and a scaling (specification of the measurement range). The measuring signal is often superimposed by interferences such as mains hum, AC noise, DC drift etc. that cannot be suppressed by lock-in technique prior to the measurement result being determined. In this case, the conversion of the measured variable into the analog sensor signal is modulated using a modulation frequency and later the digitized sensor signal is detected in a phase-sensitive manner by multiplication with a reference signal at the modulation frequency in order by a subsequent low pass filtering procedure to determine a so-called in-phase component that is directly proportional to the actual sensor signal and is processed to produce the measurement result. Since the in-phase component is dependent upon the phase difference between the modulation and the reference signal, the modulated digital sensor signal can be additionally multiplied by the reference signal, which is phase shifted by 90°, and can be subsequently low pass filtered. It is possible to determine the sensor signal in a non-phase shifted manner from the quadrature component and the in-phase component (two-phase lock-in technique).

In a measuring device in accordance with the invention, the compensation signal can advantageously perform the same digital processing steps as the sensor signal in parallel or in a time divided multiplex manner, wherein the difference between the two processed signals is only formed afterwards. Any impairment of the sensor signal as a result of shocks is therefore compensated at the sensor signal that is freed by the signal processing procedure from other interferences such as noise, drift, with the result that it is not necessary for the compensation signal to map such interferences and as a consequence the procedure of calculating the compensation signal is simplified.

According to another advantageous feature of the invention, a measuring device in accordance with the invention can be embodied as a gas analyzer having a flow-sensitive or alternating pressure-sensitive sensor element (micro flow sensor, microphone) or a thermal conductivity detector.

In accordance with the invention, compensation of shock-caused unwanted signal portions in the sensor signal is not dependent upon which part or which components of the measuring device are sensitive with respect to shocks. Shock-sensitive parts or components can be for example the chopper in an NDIR gas analyzer or optical components such as a mirror in the beam path of a gas analyzer. It is only crucial for the shocks to act upon the sensor signal.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
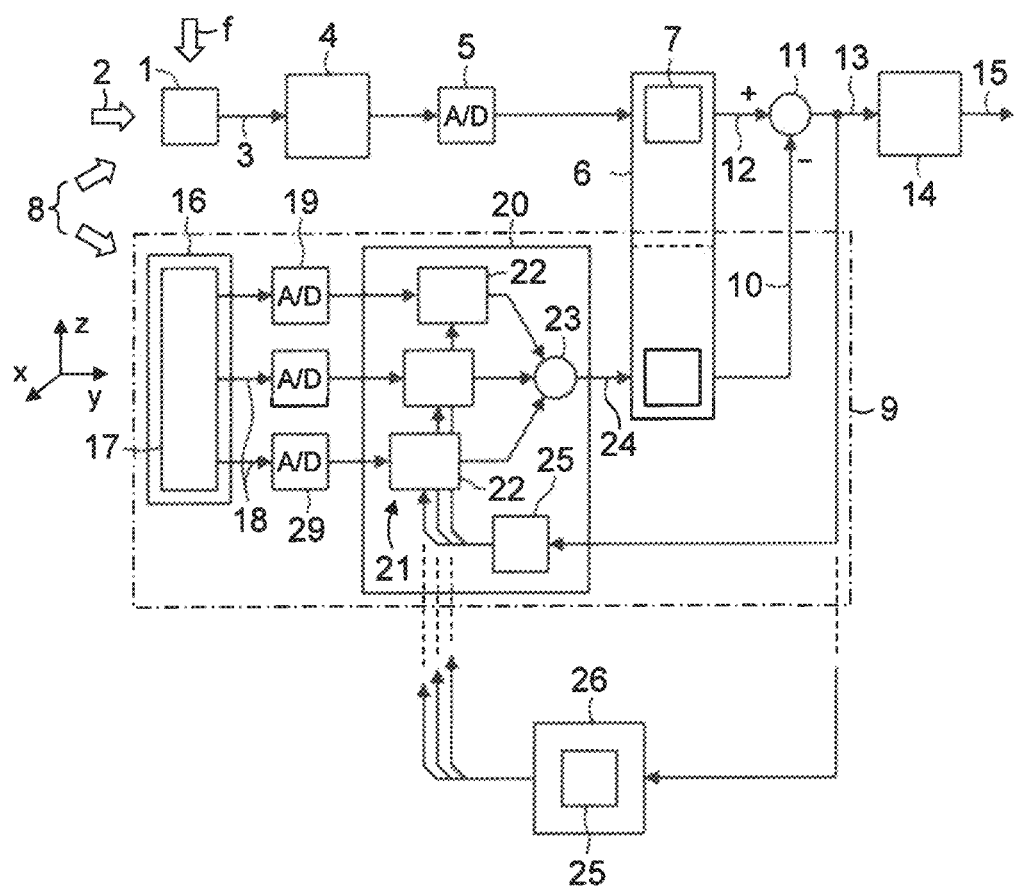
FIG. 1 is a schematic illustration of one exemplary embodiment of a measuring device in accordance with the invention.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments may be illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a schematic illustration of one embodiment of a measuring device in accordance with the invention, including a sensor 1 that converts a measured variable 2 into an analog electrical sensor signal (sensor raw signal) 3. The sensor raw signal 3 is filtered and/or amplified in an analog signal preprocessing facility 4 before the sensor signal is digitized in an analogue/digital converter 5 and further processed in a digital signal processing facility 6 by means of signal processing software, for example filtered, scaled or when the sensor signal 3 is modulated using a modulation frequency f, is demodulated by a lock-in demodulation facility 7 at this frequency.

The conversion of the measured variable 2 into the sensor signal 3 can be influenced by shocks or vibrations, indicated by arrows 8, that develop as an unwanted signal portion in the sensor signal 3. A compensation signal 10 that estimates the unwanted signal portion is therefore generated by a compensating facility 9 and is subtracted in a subtracter 11 from the processed digital sensor signal 12. A measurement result 15, i.e. a measurement value of the measured variable 2, is then determined in an evaluating facility 14 from the difference 13 of the two signals 10, 12 and output.

The compensating facility 9 includes a multi-axis MEMS inertial measuring unit 16 having a 3-axis acceleration sensor 17 that generates three different movement signals 18 corresponding to the number of axes x, y, z. The MEMS inertial measuring unit 16 can additionally include a 3-axis gyroscope that is not illustrated here and in this case can generate a total of six different movement signals.

The acceleration sensor 17 measures linear accelerations along the axes x, y, z and accordingly generates the movement signals 18 in the form of acceleration signals that can be converted by integration into velocity signals (not illustrated here). The movement signals 18 are digitized in analog/digital converters 19 and are supplied to a computer 20 having a computational model 21 that is used for the purpose of converting the movement signals 18 into the one-dimensional unwanted signal portion of the sensor signal 3, with the unwanted signal portion being caused by the shocks 8, or for the purpose of estimating the unwanted signal portion. In the case of the illustrated exemplary embodiment, the computational model 21 includes a digital filter 22 in each case for each of the three movement signals 18. The output signals of the filters 22 are added in a summing device 23 to a summation signal or output signal 24 of the computational model 21 that performs the same signal processing steps as the digitized sensor signal 3 in a further channel of the signal processing facility 6 which by way of example is here a two-channel signal processing facility 6. Alternatively, the signal processing facility 6 can be embodied in a single-channel manner and can process the two signals in a time division multiplex manner. The compensation signal 10 corresponds to an estimation of the unwanted signal portion in the processed digital sensor signal 12.

Prior to bringing the measuring device into operation or outside of the measuring operation, in the event the sensor 1 does not detect any measured variable 2, the measuring device can be exposed to vibrations one after the other on a vibration table in the direction of each of the three axes x, y, z of the acceleration sensor 17. While the vibration frequencies are tuned, a transfer function of the sensor 1 is obtained using the signal 12 and a transfer function of the MEMS inertial measuring unit 16 is obtained using the signal 10, both times inclusive of the subsequent signal processing procedure and separately for each of the three axes x, y, z. In addition it is possible while receiving the transfer functions for one of the three axes, for example the x-axis, for only the output signal of the filter 22 that obtains the movement signal 18 of the relevant axis, i.e, the x axis, to always be supplied to the summing device 23. For this purpose, the movement signals 18 that are supplied to the filters 22, the output signals of the filters 22 which are supplied to the summing device 23, or the filters 22 themselves can be individually switched on and switched off. The filter coefficients are therefore changed one after the other in each of the filters 22 with the aid of adaptation algorithms 25 in such a manner and so long until the difference 13 between the sensor signal 12 and the compensation signal 10 is minimal. This occurs, as already mentioned, one after the other for each of the filters 22 that are allocated to the three axes x, y, z of the acceleration sensor 17.

It is also possible using accordingly complex adaptation algorithms 25 to perform the procedure of setting the filters simultaneously for two or all three filters 22 respectively. Since the procedure of setting the filters 22 in the ideal case is only performed once, for example is only required when producing the measuring device and, optionally, it is only necessary to readjust in larger time intervals, the adaptation algorithms 25 can also be stored or executed in an external computing facility 26, wherein the measuring device is then connected to the external computing facility 26.

The output signals of the set filter 22 are added in the summing device 23 during the measuring operation of the measuring device, wherein the computational model 21 together with the subordinate signal processing procedure in the digital signal processing facility 6 maps the shock-caused unwanted signal portion of the processed digital sensor signal 12 into the compensation signal 10. Unwanted signal portions in the processed digital sensor signal 12, as a result of shocks, are therefore eliminated or at least reduced by forming the difference between the two signals 10, 12 in the subtractor 11.

Figure 2:
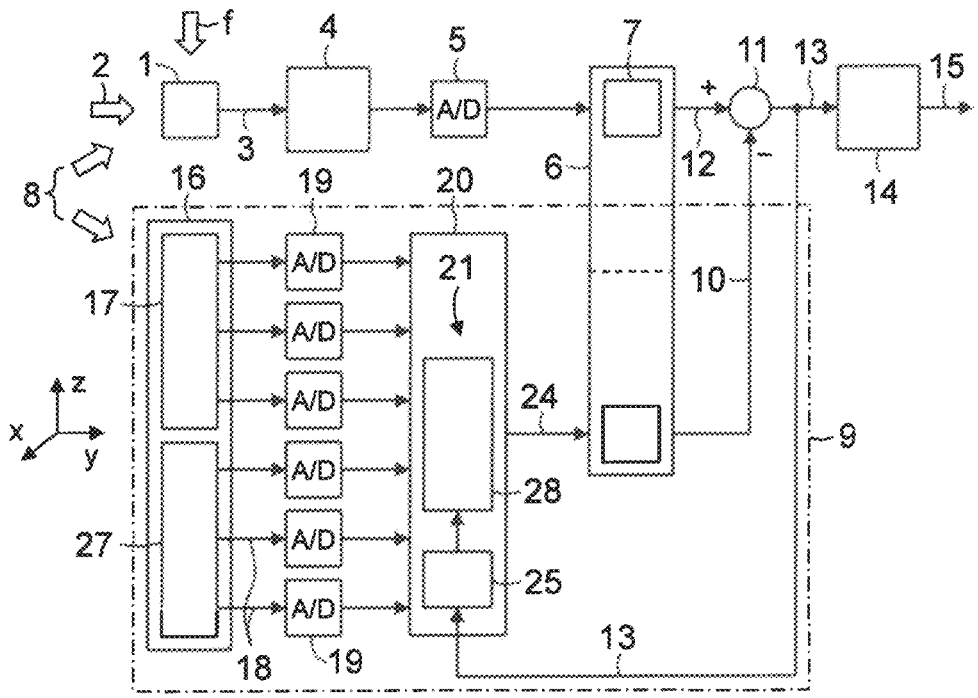
FIG. 2 is a schematic illustration of another exemplary embodiment of a measuring device in accordance with the invention.

FIG. 2 is a schematic illustration of a further example for a measuring device in accordance with the invention. Parts corresponding with those in FIG. 1 are denoted by identical reference numerals and not explained again. The description below will center on the differences between the embodiments. In this embodiment, the multi-axis MEMS inertial measuring unit 16 in addition to the 3-axis acceleration sensor 17 includes a 3-axis gyroscope 27 and accordingly the number of axes x, y, z generates a total of six different movement signals 18. While the acceleration sensor 17 measures linear accelerations along the axes x, y, z and accordingly generates movement signals 18 in the form of acceleration signals, the gyroscope 18 measures angular velocities about the axes x, y, z and accordingly generates movement signals 18 in the form of angular velocity signals.

The computational model 21 in the computer 20 includes a neural network 28 and the digitized movement signals 18 are supplied to the neural network 28 as input variables. The neural network 28 is used for the purpose of generating as an output variable 24 an estimation of the one-dimensional unwanted signal portion of the sensor signal 3, caused as a result of shocks 8. For this purpose, prior to bringing the measuring device into operation and/or outside of the measuring operation or in measuring pauses in the event the sensor 1 does not detect any measured variable 2, the neural network 28 is trained with the aid of adaptation algorithms 25 in the sense of reducing the difference 13 between the compensation signal 10, i.e. the estimation of the unwanted signal portion in the processed digital sensor signal 12, and the actual measured unwanted signal portion in the processed digital sensor signal 12. When the difference 13 between the two signals 10, 12 is zero or is below a predetermined threshold, the unwanted signal portion of the processed digital sensor signal 12 is advantageously mapped in the compensation signal 10.

Figure 3:
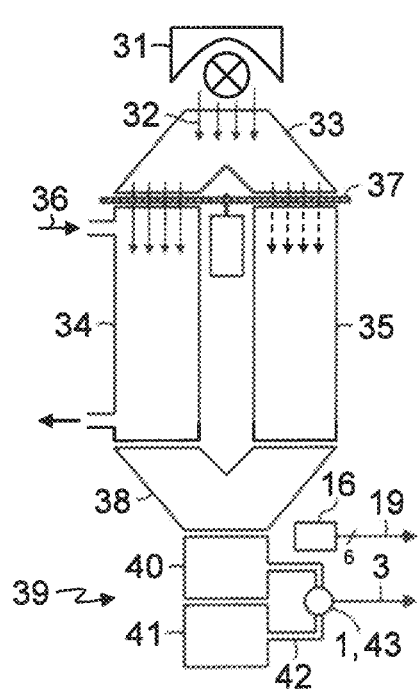
FIG. 3 is a schematic illustration of a measuring device in the form of an NDIR gas analyzer.

FIG. 3 illustrates a measuring device in the form of an NDIR gas analyzer, for example in a two-beam embodiment, in which an infrared beam 32 that is generated by an infrared radiation source 31 is divided by a beam splitter 33 into a measurement beam path by a measuring cuvette 34 and a comparison beam path by a reference cuvette 35. A measuring gas having a measuring gas component flows, as indicated by arrow 35, through the measuring cuvette 33 and the concentration of the measuring gas component is to be determined. The reference cuvette 35 is filled with a reference gas, for example nitrogen. The beam 32 is alternately blocked and allowed to pass through the measuring cuvette 34 and reference cuvette 35 by means of a modulation facility 37 which is arranged between the beam splitter 33 and the cuvettes 34, 35 and which is configured here by way of example in the form of a rotating aperture wheel or impeller wheel, with the result that infrared beams alternately pass through the two cuvettes or the two cuvettes are shaded from said infrared beams. The beam that alternately escapes the measuring cuvette 34 and the reference cuvette 35 is guided by a beam collector 38 into an optopneumatic detector system 39 that includes two chambers 40, 41 (two-layer detector) which lie one behind the other and which allow radiation to pass through and are filled with the gas component that is to be measured. The chambers 40, 41 are connected via a line 42 to the sensor 1 that is arranged therein and that generates the measuring signal 3, for example a micro flow sensor 43. The measuring signal 3 that is formed owing to the difference of the absorptions in the measuring cuvette 34 and the reference cuvette 35 has a modulation frequency f.

A MEMS inertial measuring unit 16 is arranged in dose proximity to the optopneumatic detector system 39 and the movement signals 19 and the sensor signal 3 of said MEMS inertial measuring unit are processed as described above with reference to FIG. 1 and are demodulated at the frequency f. Since the measuring signal 3 in addition to the modulation frequency f also contains an unwanted signal portion having the double modulation frequency $2f$, said unwanted signal portion being provided by the sum of the absorptions in the measuring cuvette 34 and the reference cuvette 35, it is possible to additionally perform a phase-sensitive demodulation at the double modulation frequency $2f$ in order to determine a diagnosis value from the in-phase component and quadrature component that are obtained in this case or to standardize the measurement result with the aid of such a diagnosis value.

Figure 4:
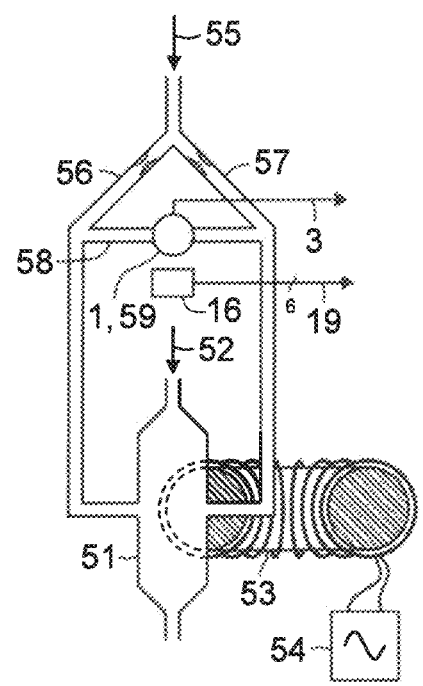
FIG. 4 is a schematic illustration of a measuring device in the form of a gas analyzer that operates according to a paramagnetic alternating pressure method.

FIG. 4 illustrates in an exemplary manner the measuring device in the form of a gas analyzer that operates according to the paramagnetic alternating pressure method. This gas analyzer has a measuring chamber 51 that a measuring gas 52 flows through and the oxygen portion of said measuring gas is to be determined. A part of the measuring chamber 51 is between the pole shoes of an alternating current-supplied electromagnet 53 in the magnetic field that is generated by said electromagnet. The electromagnet 53 is actuated by a current source or voltage source 54 using alternating current. A reference gas 55 that is necessary for achieving the measuring effect is supplied to the measuring chamber 51 by two identical ducts 56, 57, wherein one of the two comparative gas flows encounters the measuring gas 52 in the region of the magnetic field. Since oxygen molecules are moved in the direction of higher field strengths on account of their paramagnetic property in the magnetic field, an alternating pressure difference having the frequency f arises between the comparative gas flows in the ducts 56, 57 and the frequency f is double the frequency (½ f) of the alternating current. This causes an alternating flow in a connecting duct 58 between the two ducts 56, 57 and said alternating flow is detected by means of the sensor 1 here in the form of a micro flow sensor 59 and is converted into the electrical measuring signal 3.

A MEMS inertial measuring unit 16 is arranged in close proximity to the micro flow sensor 59 and the movement signals 19 and the sensor signal 3 of the MEMS inertial measuring unit are processed as described above with reference to FIG. 1 and are demodulated at the frequency f. Since the sensor signal 3 having the frequency f can include an unwanted signal portion having the frequency ½ f of the alternating current through transformational coupling between the electromagnet 53 and the current sensor 59 or the subordinate signal processing procedure, an additional phase-sensitive demodulation at the half modulation frequency ½ f may be performed in order to determine a diagnosis value from the in-phase component and quadrature component that are obtained in this case or to standardize the measurement result with the aid of such a diagnosis value.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed is:

1. A shock-sensitive measuring device, comprising:
   a sensor generating a sensor signal in dependence upon a detected measured variable;
   a compensating facility generating a compensation signal in response to detected shocks of the measuring device; and
   an evaluating facility generating a measurement result from a difference between the sensor signal and the compensation signal,
   wherein the compensating facility comprises
      a multi-axis MEMS inertial measuring unit including an acceleration sensor alone or together with a gyroscope and configured to generate a plurality of movement signals in correspondence to a number of axes, and
      a computer including a computational model embodied and trained to model an unwanted signal portion of the sensor signal in response to the shocks caused by the movement signals and to output the unwanted signal portion as a compensation signal, said computational model being trained in such a manner that absent a measured variable, the difference between the sensor signal and the compensation signal is zero or is below a predetermined threshold.

2. The measuring device of claim 1, wherein the computational model includes a neural network.

3. The measuring device of claim 1, wherein the computational model comprises
   a plurality of digital filters for the movement signals in one-to-one correspondence, each said digital filter having adjustable filter coefficient and trained via a setting of the filter coefficient to model the unwanted signal portion of the sensor signal in correlation with an associated one of the movement signal, and
   a summing device configured to add output signals of the digital filters during a measuring operation so as to generate the compensation signal.

4. The measuring device of claim 1, further comprising a signal processing facility configured to identically process the sensor signal and the compensation signal prior to generating the difference.

5. The measuring device of claim 4, further comprising a modulation facility configured to trigger a modulation of the sensor signal using a modulation frequency, said signal processing facility including a lock-in demodulation facility to demodulate the sensor signal and the compensation signal at the modulation frequency.

6. The measuring device of claim 1, wherein the measuring device is embodied as a gas analyzer having a flow-sensitive or alternating pressure-sensitive sensor element or a thermal conductivity detector.

* * * * *